US010722199B2

(12) United States Patent
Hiroike

(10) Patent No.: US 10,722,199 B2
(45) Date of Patent: Jul. 28, 2020

(54) RADIOGRAPHIC APPARATUS AND RADIOGRAPHIC SYSTEM

(71) Applicant: CANON KABUSHIKI KAISHA, Tokyo (JP)

(72) Inventor: Taro Hiroike, Yamato (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 341 days.

(21) Appl. No.: 15/802,200

(22) Filed: Nov. 2, 2017

(65) Prior Publication Data

US 2018/0140268 A1 May 24, 2018

(30) Foreign Application Priority Data

Nov. 7, 2016 (JP) .................. 2016-217078

(51) Int. Cl.
*A61B 6/00* (2006.01)
*H04N 5/343* (2011.01)
*H04N 5/32* (2006.01)
*H04N 5/378* (2011.01)

(52) U.S. Cl.
CPC ............ *A61B 6/461* (2013.01); *A61B 6/4233* (2013.01); *A61B 6/4283* (2013.01); *A61B 6/542* (2013.01); *A61B 6/545* (2013.01); *A61B 6/563* (2013.01); *H04N 5/32* (2013.01); *H04N 5/343* (2013.01); *H04N 5/378* (2013.01)

(58) Field of Classification Search
None
See application file for complete search history.

(56) References Cited

U.S. PATENT DOCUMENTS 4,096,474 A * 6/1978 Greer ................. G08B 13/1663
340/425.5
2013/0140467 A1* 6/2013 Kitano ............... H04N 5/37213
250/393

FOREIGN PATENT DOCUMENTS

| JP | 60-53125 A | 3/1985 |
| JP | 2005-013272 A | 1/2005 |
| JP | 2012-100962 A | 5/2012 |

* cited by examiner

*Primary Examiner* — Edwin C Gunberg
(74) *Attorney, Agent, or Firm* — Canon U.S.A., Inc. IP Division

(57) ABSTRACT

A radiographic apparatus includes a plurality of notifying units, each including a different way to provide notification, and a switching unit that switches at least one of the notifying units to be used to provide notification based on an arrangement of or imaging mode of the radiographic apparatus.

11 Claims, 8 Drawing Sheets

SP       SP+LED      LED

RADIOGRAPHIC APPARATUS AND RADIOGRAPHIC SYSTEM

BACKGROUND

Field

The present disclosure relates to a radiographic apparatus including a plurality of notifying units and a radiographic system.

Description of the Related Art

Radiographic apparatuses using a flat panel detector (FPD) made of a semiconductor material have been widespread in the medical field. An increase in the number of functions performed by the radiographic apparatus has enhanced importance of a notifying unit as a user interface of a radiographic system including the radiographic apparatus. The notifying unit notifies a user of a state of the radiographic apparatus.

Japanese Patent Application Laid-Open No. 2005-013272 discusses an X-ray imaging apparatus that uses sound, vibration, or light to notify a user of a drive state of an X-ray detector. Japanese Patent Application Laid-Open No. 2012-100962 discusses a radiographic imaging system including an electronic cassette that includes an indicator and a speaker. The indicator displays on and off of power supply, and the speaker outputs sound to notify a position in an imaging room.

In radiographic image capturing, a radiographic apparatus is used in various states. For example, an image can be captured in a state in which the radiographic apparatus is set on a dedicated tray, and an image can be captured in a state in which the radiographic apparatus is placed under a subject lying on a bed. In each of such cases, even if the radiographic apparatus includes a display unit, there is a possibility that a user may not be able to acquire necessary information at appropriate timing since the user cannot check the display unit.

The radiographic apparatus can be used in a room, such as an operating room or an intensive care unit, where there are notifying sounds from other electronic devices. In such a case, a user may not be able to acquire appropriate information since the user cannot distinguish between notifying sound from the radiographic apparatus and notifying sound from the other electronic devices. The use of sound may not be permitted in some environment. Hence, an appropriate notifying unit differs depending on environment and an image capturing method.

There is a related-art imaging system including a plurality of notifying units. However, such a related-art imaging system cannot switch these notifying units, causing difficulty in appropriately dealing with various imaging conditions.

SUMMARY

According to an aspect of the present disclosure, a radiographic apparatus includes a plurality of notifying units, each including a different way to provide notification, and a switching unit configured to switch at least one of the plurality of notifying units to be used to provide notification.

Further features will become apparent from the following description of exemplary embodiments with reference to the attached drawings.

DESCRIPTION OF THE EMBODIMENTS

Hereinafter, exemplary embodiments are described in detail with reference to the drawings. In each of the exemplary embodiments, imaging using X-rays is described. However, the radiation used in the exemplary embodiments is not limited to the X-rays. The radiation includes alpha rays ($\alpha$-rays), beta rays ($\beta$-rays), gamma rays ($\gamma$-rays), and various particle beams.

Figure 1:
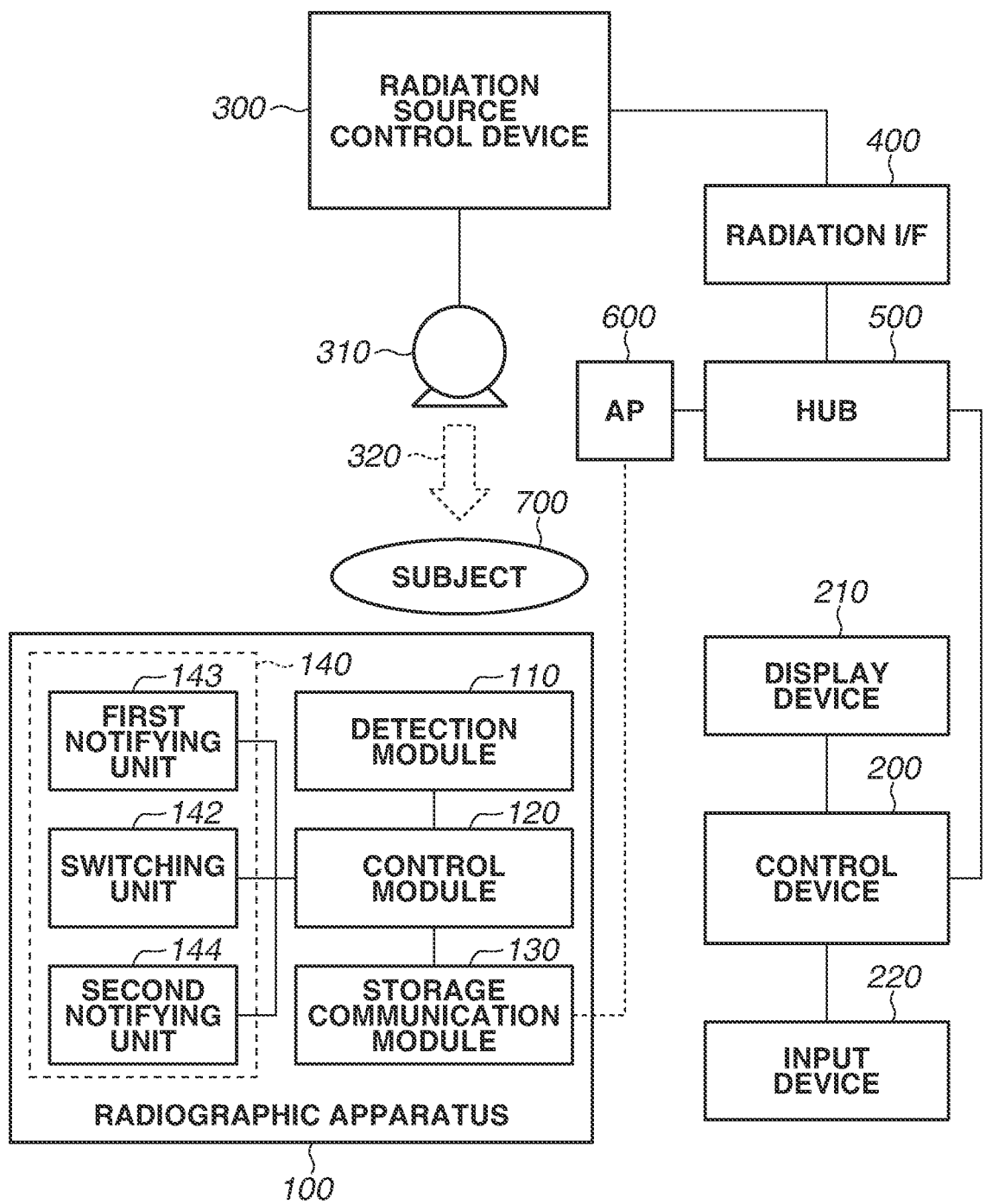
FIG. 1 is a block diagram illustrating a radiographic system according to a first exemplary embodiment.

FIG. 1 illustrates a schematic configuration of a radiographic system 10 according to a first exemplary embodiment. The radiographic system 10 includes a radiographic apparatus 100. The radiographic apparatus 100 detects radiation 320 emitted from a radiation source 310 and transmitted through a subject 700, thereby acquiring radiographic image data of the subject 700. An FPD is suitable as the radiographic apparatus 100.

The radiographic apparatus 100 includes at least a detection module 110 and a control module 120. The detection module 110 converts the detected radiation into electric signals. The converted electric signals are digitized and transmitted to the control module 120. After performing various signal processing on the signals, the control module 120 transmits the resultant signals to a storage communication module 130. The storage communication module 130 stores the received signals in a storage device. Herein, the signals are stored as image data. The storage communication module 130 transmits the signals to an external control device 200 via a communication interface.

The control device 200 can be connected to a display device 210, such as a display for displaying a control menu and captured-image data, and an input device 220, such as a mouse and a keyboard, from which various inputs are made.

The control module 120 controls image data processing as well as the radiographic apparatus 100. For example, the control module 120 controls driving of the detection module 110 and input processing performed from an operation module 140. The operation module 140 includes a plurality of notifying units 143 and 144 having a plurality of different notifying manners and a switching unit 142. The switching unit 142 is disposed to switch a notifying unit out of the plurality of notifying units 143 and 144. The switching unit 142 can be, for example, a slide switch, a button switch, or a touch panel. In the present exemplary embodiment, the switching unit 142 is disposed in the radiographic apparatus 100. However, the switching unit 142 can be disposed in the control device 200. In such a case, a desired notifying unit can be selected from a menu displayed on the display device 210 connected to the control device 200 by an operation on the input device 220.

A personal computer (PC) or a workstation is used as the control device 200. The control device 200 controls imaging modes and entire operation of the radiographic system 10. The control device 200 acquires image data from the radiographic apparatus 100 to perform image processing on the image data.

The radiographic apparatus 100 and the control device 200 communicate with each other via a wireless local area network (LAN) via an access point (AP) 600. The radiographic apparatus 100 or the control device 200 can also serve as an access point. In such a case, the radiographic apparatus 100 and the control device 200 directly communicate with each other without the external AP 600. Alternatively, the radiographic apparatus 100 and the control device 200 can be connected by a wireless communication unit using, for example, Bluetooth® or a wired communication unit using, for example, Ethernet.

A radiation interface unit (radiation I/F) 400 is disposed between the control device 200 and a radiation source control device 300. The radiation I/F 400 includes a circuit for mediating communication between the radiographic apparatus 100 and the radiation source control device 300, and, for example, relays exchange of synchronizing signals. The radiation I/F 400 monitors a state of the radiographic apparatus 100 and a state of the radiation source control device 300 so that irradiation timing at which radiation is emitted from the radiation source 310 can be adjusted based on the state of the radiographic apparatus 100. The radiation I/F 400 is connected to the control device 200 to relay exchange of various control signals and information.

The radiation I/F 400 is connected to the control device 200 by Ethernet via a HUB 500. The HUB 500 connects a plurality of network devices. The AP 600 is connected to the HUB 500 so that the HUB 500 is also connected to the radiographic apparatus 100 via the wireless LAN.

In a case where an image is automatically captured by the radiographic system 10 when the radiographic apparatus 100 detects radiation from the radiation source 310, the radiation I/F 400 is not necessary. The present exemplary embodiment can also be applied to such an asynchronous system.

Figure 2:
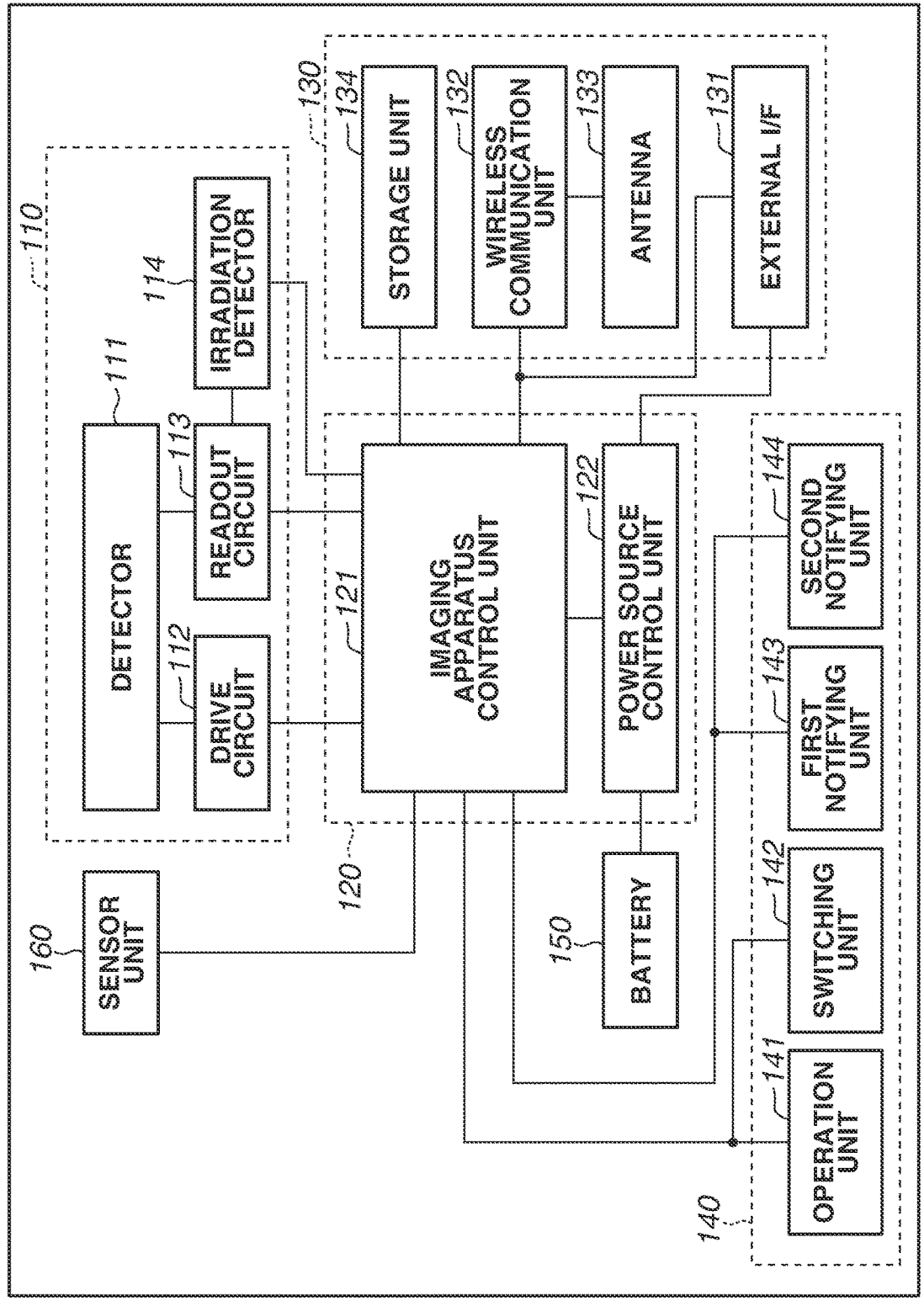
FIG. 2 is a block diagram illustrating an exemplary configuration of a radiographic apparatus.

FIG. 2 is a schematic diagram illustrating an exemplary configuration of the radiographic apparatus 100.

An imaging apparatus control unit 121 controls operation of the radiographic apparatus 100. The imaging apparatus control unit 121 and a power source control unit 122 form the control module 120.

The power source control unit 122 controls a power source for operation of the radiographic apparatus 100. The power source control unit 122 receives power supply from a battery 150 or an external interface (an external I/F) 131 to generate various power necessary for the operation of the radiographic apparatus 100, and supplies the power to each unit of the radiographic apparatus 100. The power source control unit 122 can include a function of controlling charging of the battery 150.

Figure 6:
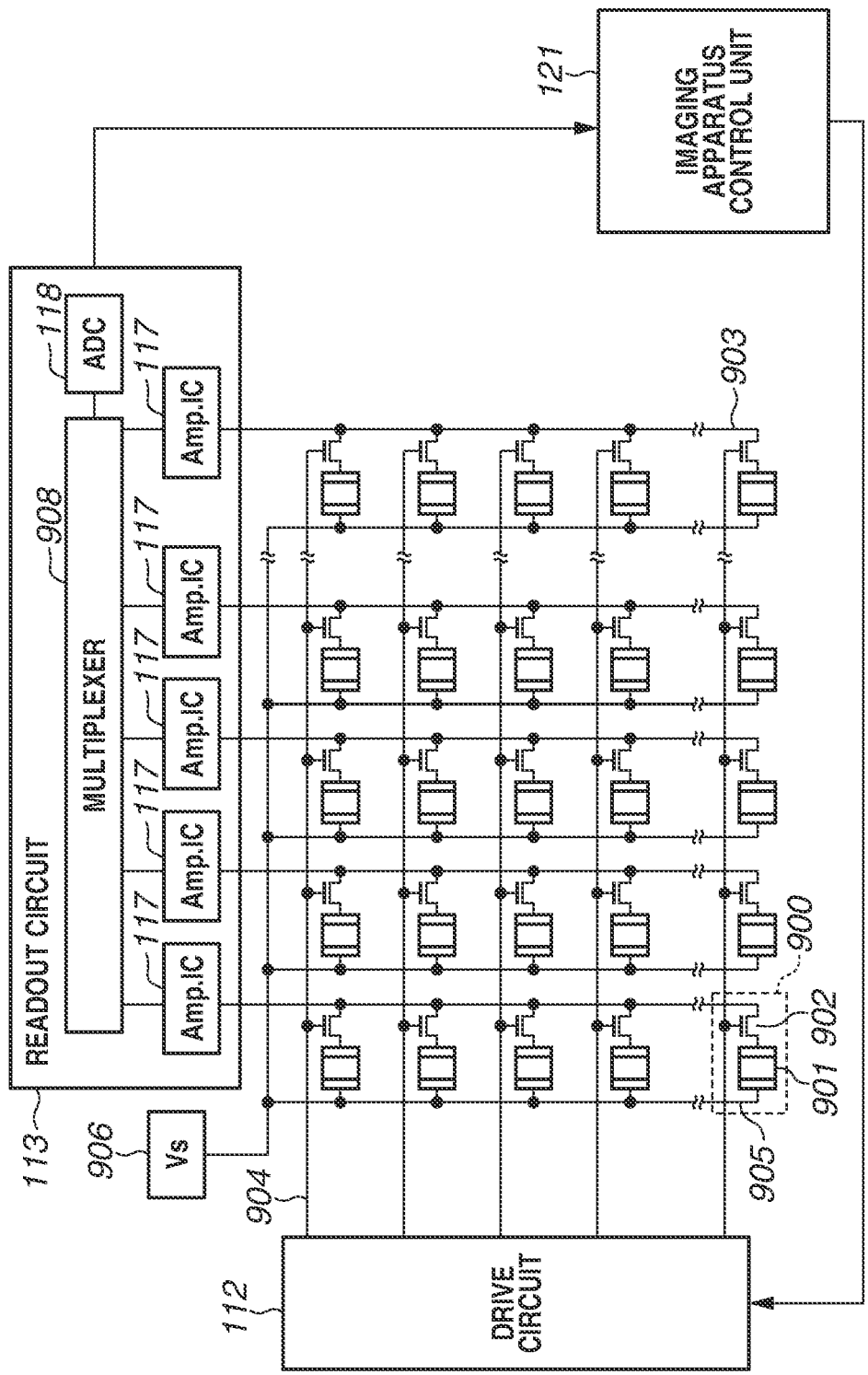
FIG. 6 is a block diagram illustrating an exemplary configuration of a detection module of the radiographic apparatus.

The detection module 110 includes a detector 111, a drive circuit 112, and a readout circuit 113. As illustrated in FIG. 6, the detector 111 includes a plurality of imaging pixels 900 that are arranged in a matrix. The imaging pixel 900 includes a first conversion element 901 for converting radiation into electric signals and a first switch 902 arranged between the first conversion element 901 and a signal line 904. The first conversion element 901 includes a scintillator for converting radiation into light and a photoelectric conversion element for converting the light into electric signals.

In a case of an asynchronous type, the detection module 110 can include an irradiation detector 114. For example, the irradiation detector 114 detects a change in an electric current (a bias current) flowing in a bias line 905. That is, an input signal generated by irradiation of the detector 111 with radiation is transmitted to the irradiation detector 114 and a change in an amount of the bias current in the course of the radiation irradiation is detected, so that the start of the radiation irradiation is determined.

The imaging apparatus control unit 121 performs processing for correcting an image defect and an offset and processing for reducing various noises with respect to digital image data that has been input. The image data processed by the imaging apparatus control unit 121 is transmitted to the storage communication module 130. The storage communication module 130 includes a storage unit 134, a wireless communication unit 132, and the external I/F 131.

The storage unit 134 stores the image data processed by the imaging apparatus control unit 121 with information associated with the image data. The information associated with the image data includes information about a radiographed subject, information about a user, information about a radiographed portion, information about a date and time on which the radiography is performed, and unique identification (ID) by which the radiographic image is identified. If an image is captured by an asynchronous system, the information associated with the image data can include information used in radiation detecting determination.

The wireless communication unit 132 wirelessly transmits data, such as the image data, stored in the storage unit 134 to a device, such as the external control device 200. An antenna 133 is connected to the wireless communication unit 132. The image data processed by the imaging apparatus control unit 121 can be transmitted to an external unit via the wireless communication unit 132. In such a case, the image data can be stored in the storage unit 134 at the same time as the transmission of the image data to the external unit. The transmission of the image data to a device, such as the control device 200, can be performed by wired communication via the external I/F 131 instead of by the wireless communication unit 132.

The operation module 140 includes an operation unit 141 that is operated by a user, and the plurality of notifying units 143 and 144. The notifying units 143 and 144 include a display unit (a first notifying unit), such as a liquid crystal display (LCD) and a light emitting diode (LED), and a sound generating unit (a second notifying unit), such as a speaker. The display unit as a notifying unit performs notification by using light, whereas the sound generating unit as a notifying unit performs notification by using sound. The operation module 140 includes the switching unit 142 for switching a notifying unit to be used or a combination of notifying units to be used from the plurality of notifying units. The operation unit 141, the switching unit 142, and the notifying units 143 and 144 are connected to the imaging apparatus control unit 121.

The sensor unit 160 detects a state of an image capturing unit. The sensor unit 160 can include one or more of an optical sensor and a pressure sensor. A signal output from the sensor unit 160 is input to the imaging apparatus control unit 121.

Figure 3:
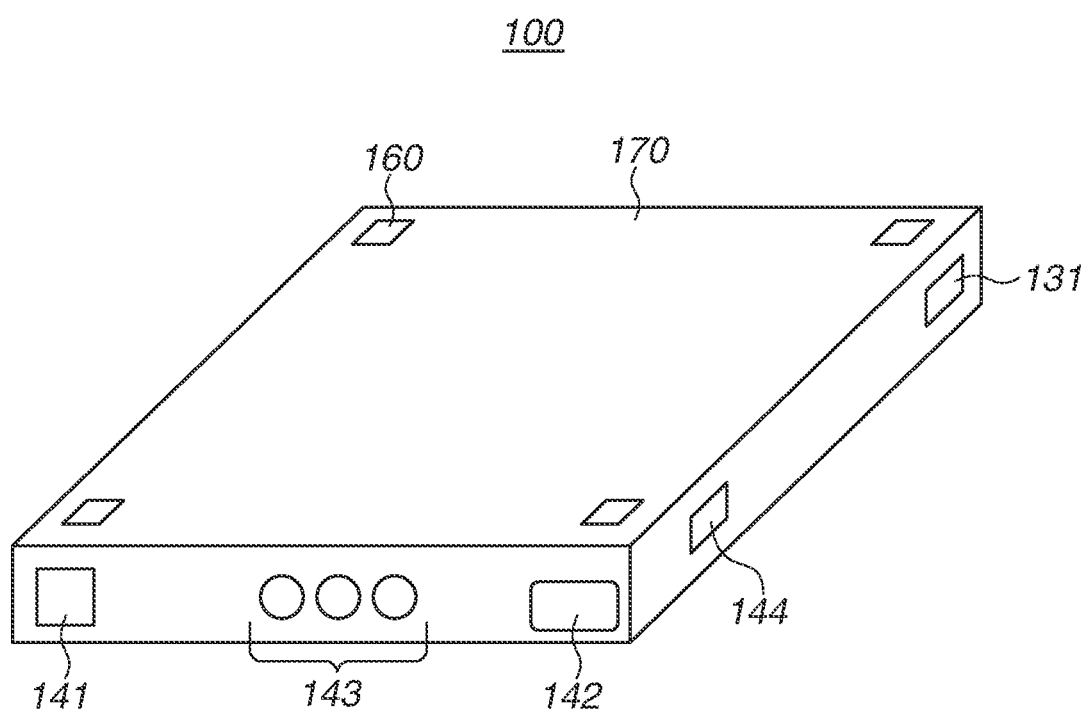
FIG. 3 is a schematic diagram illustrating an exemplary external configuration of the radiographic apparatus.

FIG. 3 is a schematic diagram illustrating an exemplary external configuration of the radiographic apparatus 100.

The operation unit 141, the notifying units 143 and 144, the switching unit 142, and the external I/F 131 are arranged on a side surface of the radiographic apparatus 100. In the present exemplary configuration, the notifying unit 143 is a display unit using an LED and the notifying unit 144 is an opening of a speaker. While the notifying units 143 and 144 are preferably arranged on the side surface of the radiographic apparatus 100, the notifying units 143 and 144 can be arranged on a back side or a side into which radiation enters.

The operation unit 141 includes a button or a dial, a slide switch, a touch sensor, and a touch panel. The operation unit 141, serving as an interface, receives an instruction from the user so that various operations of the radiographic apparatus 100 are performed. In the present exemplary configuration, the operation unit 141 includes a switch that functions as a power button.

The sensor unit 160, serving as an input opening of an optical sensor, is disposed in each of four corners of an irradiation surface. A pressure sensor is disposed inside the radiographic apparatus 100 such that pressure applied to the irradiation surface can be detected.

Figure 4:
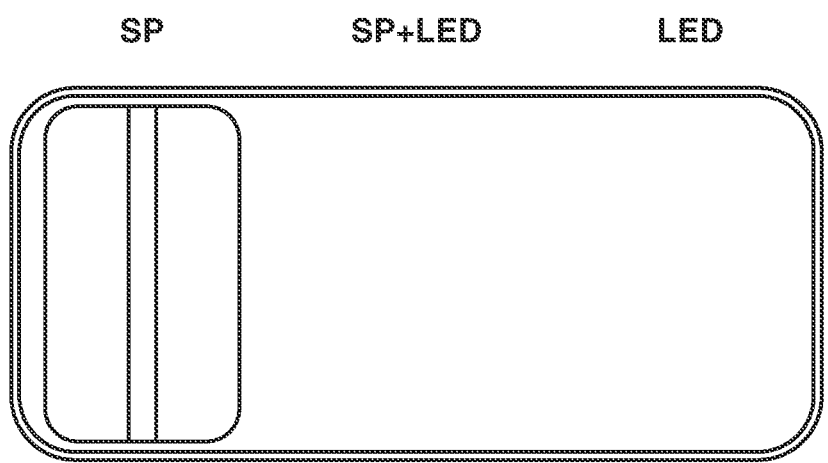
FIG. 4 is a schematic diagram illustrating an exemplary configuration of the switching unit of the radiographic apparatus.

FIG. 4 is a schematic diagram illustrating an exemplary configuration of the switching unit 142 of the radiographic apparatus 100. The switching unit 142 includes a slide switch. The switching unit 142 switches, based on the position of the slide switch, whether to use only the speaker, only the LED, or both the speaker and the LED.

The user operates the switching unit 142 according to an arrangement state of the radiographic apparatus 100, thereby switching a notifying unit to be used in image capturing. For example, in one case, the user can hold the radiographic apparatus 100 in the user's hand to operate the radiographic apparatus 100. In such a case, the user operates the switching unit 142 such that both of the speaker and the LED are used. In another case, the radiographic apparatus 100 can be placed under a subject. In such a case, the user cannot see display of the LED. Thus, the user switches the switching unit 142 before capturing an image such that only the speaker is used. Accordingly, an unnecessary notifying unit is turned off, and thus, power consumption is reduced.

Figure 5:
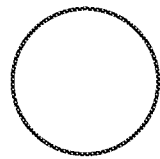
FIG. 5 is a diagram illustrating a display on the radiographic apparatus indicating a selected notifying unit.
Figure 5:
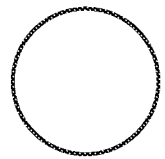
Figure 5:
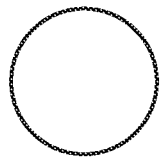

While the present exemplary embodiment has been described using an example case in which the switching unit 142 is disposed in the radiographic apparatus 100, in another exemplary embodiment, the notifying units can be switched via the control device 200. In such a case, as illustrated in FIG. 5, a display for indicating which notifying unit is being selected is preferably provided on the radiographic apparatus 100.

In another exemplary embodiment of the radiographic apparatus 100, a notifying unit to be used is switched based on outputs of various sensors arranged inside the radiographic apparatus 100. In the radiographic apparatus 100, as illustrated in FIG. 3, an optical sensor, as the sensor unit 160, is disposed in each of four corners of an irradiation surface 170 that is irradiated with radiation. Such an optical sensor can measure intensity of ambient light with which a position of the corner is irradiated.

If an intensity of the ambient light is less than or equal to a threshold value, it is determined that the radiographic apparatus 100 is in a state of being set inside a dedicated tray provided on a table or a stand for image capturing, or the radiographic apparatus 100 in a state of being placed under a subject. In such a case, a notifying unit is automatically switched such that a display using the LED is turned off and only the speaker is used.

Similarly, a pressure sensor that is disposed inside the radiographic apparatus 100 and that measures a load applied to a radiation irradiation surface can be used to determine a switching condition of the notifying unit. In this case, if a pressure exceeding a predetermined threshold value is applied, it is determined that the radiographic apparatus 100 is in a state of being placed under a subject. Thus, a notifying unit is automatically switched such that a display using the LED is turned off and only the speaker is used.

If a notifying unit is automatically switched, an imaging apparatus control unit 121 serves as a switching unit. If the radiographic system 10 includes the switching unit 142, which is used when a user manually selects and switches a notifying unit, a result of the selection made using the switching unit 142 is prioritized.

In yet another exemplary embodiment of the radiographic apparatus 100, the radiographic apparatus 100 includes a radiation irradiation detection mode in which the radiographic apparatus 100 detects the start of radiation irradiation to capture an image. Electric current information of a bias line is used as an input signal for detection of the start of irradiation. If a sample value of the electric current input to a radiation irradiation detector exceeds a predetermined threshold value, the radiographic apparatus 100 can determine that radiation irradiation has been started.

In a case where an interface unit is used to capture an image in response to a radiation source control device 300, radiation irradiation is controlled so as not to be performed at timing other than the timing in which image capturing can be performed. An image can be captured in a radiation automatic detection mode. In such a case, even if the radiographic apparatus 100 or the radiographic system 10 is not in an appropriate image capturing state, radiation irradiation can be performed. Since radiation is harmful to human body, the human body should not be irradiated with radiation at an inappropriate timing. Accordingly, a system capturing an image in the radiation automatic detection mode needs to notify a user of necessary information in a more intelligible manner than a system capturing an image by using an interface unit.

The term "necessary information" used herein includes information about a state of an image capturing unit. For example, a state in which the radiographic apparatus has become ready for image capturing or a state in which the radiographic apparatus has become unable to capture an image. A state allowing image capturing to be performed can have a time limit. In such a case, a notifying unit can be used to notify the user of the time limit according to a remaining time. The radiographic system can be set such that an image is captured at a time when radiation irradiation is detected and then image capturing is started or at a time when radiation irradiation is finished. The radiographic system can be set such that an image is captured at a certain accumulation time. In such a case, the user can be notified at a time when the accumulation is finished. The user can be preferably notified at a time when processing, such as readout processing, performed during or subsequent to the accumulation and image data transfer processing is completed to prevent malfunction due to external impact during such processing.

In the present exemplary embodiment of the radiographic apparatus 100, if an image is captured in a radiation automatic detection mode, the imaging apparatus control unit 121 automatically switches a notifying unit to a speaker to reliably notify a user of necessary information, even in a state in which the user cannot check a display, such as a LED, disposed on the radiographic apparatus 100. If an image is not captured in the radiation automatic detection mode, i.e., if an image is captured when an irradiation start signal is received from the radiation generating device 310, the user is notified by one or more of the speaker and the LED.

If the radiographic system 10 of the first exemplary embodiment includes a notifying unit switching unit where a notifying unit is manually selected and switched, a result of the selection made using such a unit is prioritized.

The radiographic system 10 according to a second exemplary embodiment detects an amount of radiation or an integrated dose. Such detection enables an image to be captured in a mode including an auto exposure control (AEC) function of stopping radiation irradiation if a radiation dose reaches a predetermined dose.

Figure 7:
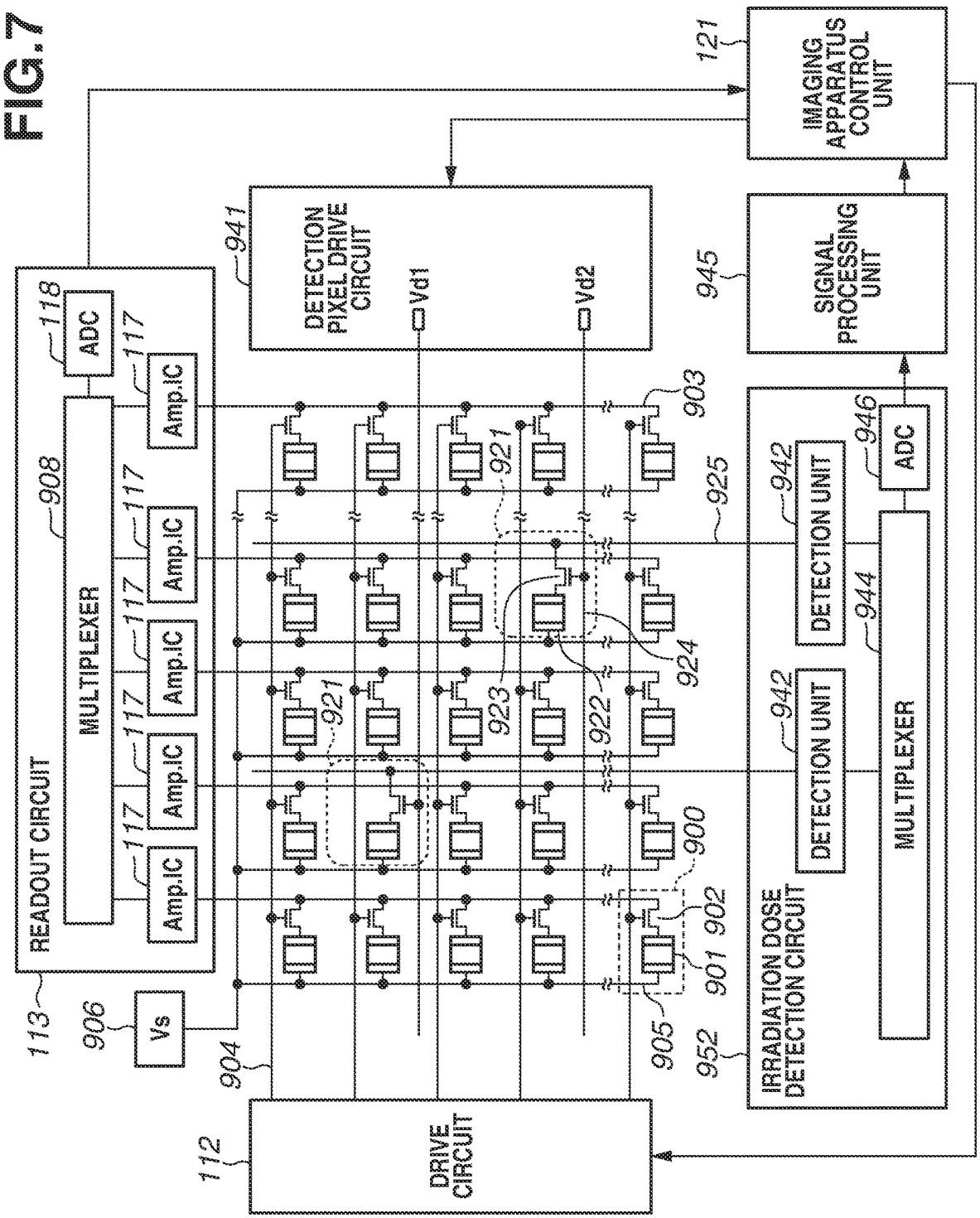
FIG. 7 is a block diagram illustrating another exemplary configuration of a detection module of the radiographic apparatus.

FIG. 7 is a diagram illustrating another exemplary configuration of the detection module 110 of the radiographic apparatus 100. A description is provided of a portion for detecting a radiation dose or an integrated dose by referring to the difference(s) between FIG. 7 and FIG. 6.

The detector 111 includes a plurality of pixels, including a plurality of imaging pixels 900, for acquiring a radiographic image and at least one detection pixel 921 for detecting a radiation dose. The imaging pixel 900 includes a first conversion element 901 for converting radiation into electric signals and a first switch 902 arranged between a signal line 903 and the first conversion element 901. The detection pixel 921 includes a second conversion element 922 for converting radiation into electric signals and a second switch 923 arranged between a detection signal line 925 and the second conversion element 922.

Both the first conversion element 901 and the second conversion element 922 include a scintillator for converting radiation into light and a photoelectric conversion element for converting the light into electric signals. In general, the scintillator is formed in a sheet shape to cover an imaging region including a plurality of imaging pixels, and is shared by the plurality of imaging pixels. Both the first conversion element 901 and the second conversion element 922 can include a conversion element for directly converting radiation into light.

Both the first switch 902 and the second switch 923 include a thin-film transistor (TFT) including an active region made of a semi-conductor, such as amorphous silicon or polycrystalline silicon (preferably polycrystalline silicon).

The first conversion element 901 includes a first electrode and a second electrode that are connected to a first main electrode of the first switch 902 and a bias line 905, respectively. Herein, one bias line 905 extends in a column direction and is commonly connected to the second electrode of each of the plurality of first conversion elements 901 arrayed in the column direction. The bias line 905 receives a bias voltage Vs from a power supply circuit 906. The first switch 902 of each of the plurality of imaging pixels 900 forming one column includes a second main electrode that is connected to one signal line 903. The first switch 902 of each of the plurality of imaging pixels 900 forming one row includes a control electrode that is connected to one signal line 904.

The plurality of signal lines 903 is connected to the readout circuit 113. Herein, the readout circuit 113 includes a plurality of amplifier integrated circuits (amplifier ICs) 117, a multiplexer 908, and an analog digital converter (hereinafter, an ADC) 118. Each of the signal lines 903 is connected to the corresponding amplifier IC 117 out of the plurality of amplifier ICs 117. One signal line 903 corresponds to one amplifier IC 117. The amplifier IC 117 includes a differential amplifier. The multiplexer 908 selects a plurality of amplifier ICs 117 in predetermined order and supplies signals from the selected amplifier ICs 117 to the ADC 118. The ADC 118 converts the supplied signals into digital signals and outputs the digital signals. An imaging apparatus control unit 121 receives the digitally converted image information.

The second conversion element 922 includes a first electrode and a second electrode that are connected to a first main electrode of the second switch 923 and the bias line 905, respectively. The second switch 923 includes a second main electrode that is electrically connected to the detection signal line 925. The second switch 923 includes a control electrode that is electrically connected to a drive line 924. At least one detection pixel 921 is connected to one detection signal line 925. The drive line 924 is driven by a detection pixel drive circuit 941. At least one detection pixel 921 is connected to one drive line 924.

The detection signal line 925 is connected to an irradiation dose detection circuit 952. The irradiation dose detection circuit 952 includes a plurality of detection units 942, a multiplexer 944, and an AD converter (ADC) 946. Each of the detection signal lines 925 is connected to the corresponding detection unit 942 out of the plurality of detection units 942. One detection signal line 925 corresponds to one detection unit 942. The detection unit 942 includes a differential amplifier. The multiplexer 944 selects a plurality of detection units 942 in predetermined order and supplies signals from the selected detection units 942 to the AD converter 946. The AD converter 946 converts the supplied signals into digital signals and outputs the digital signals.

A signal processing unit 945 outputs, based on the output of the irradiation dose detection circuit 952 (the ADC 946), information indicating a dose of radiation with which the radiographic apparatus 100 is irradiated. The imaging apparatus control unit 121 controls a drive circuit 112, the detection pixel drive circuit 941, and the readout circuit 113 based on the information from the signal processing unit 945. The imaging apparatus control unit 121 controls the start and the end of an accumulating operation (performed by the imaging pixels 900 for accumulation of electric charges corresponding to emitted radiation) based on the information from the signal processing unit 945. The imaging apparatus control unit 121 generates a radiation irradiation stop signal and transmits the radiation irradiation stop signal to the radiation source control device 300 via a radiation interface to stop the radiation irradiation.

In general, when a radiographic image is captured, a necessary irradiation dose varies based on a condition (e.g., physique) of a subject. Normally, a user sets an appropriate irradiation dose based on the condition. However, there is a possibility that a variation in the irradiation dose or a setting error can be made by the user. In such a case, an image is captured with an excessively high or low dose of radiation, and thus a desired image cannot be acquired.

Since the AEC function solves such issues, the use of the AEC function enables images to be stably acquired regardless of a condition of a subject. When an image is captured using the AEC function, a maximum conceivable irradiation time or dose is often set to deal with conditions of various subjects. Accordingly, in a case where the AEC function does not work as it is anticipated, or in a case where a dose is not enough to stop the radiation irradiation, an image with desired quality is not acquired and radiation is excessively emitted. Thus, preferably, the user is notified that the AEC function has worked as anticipated.

In an exemplary embodiment of the radiographic apparatus 100 when an image is captured in a mode using an AEC function, an imaging apparatus control unit 121 automatically switches a notifying unit such that a speaker reliably notifies a user of necessary information even in a state in which the user cannot check a display, such as a LED, disposed on a radiographic apparatus 100. When an image is captured in a mode in which the AEC function is not used, the user is notified by one or more of the speaker and the LED.

If the radiographic system 10 of the second exemplary embodiment includes a switching unit 142 that is used when a user manually selects and switches a notifying unit, a result of the selection made using the switching unit 142 is prioritized.

In a radiographic system 10 according to a third exemplary embodiment, a radiographic apparatus 100 can capture an image in a stand-alone mode in which a radiographic apparatus 100 successively captures images on a stand-alone basis without communication with a control device 200. A user can select the stand-alone mode by operating an imaging mode selection unit (not illustrated). The imaging mode selection unit can be disposed in the radiographic apparatus 100, or switched by operation of a control device.

A plurality of pieces of image data captured in the stand-alone mode is sequentially stored in a storage unit inside the radiographic apparatus 100. Herein, identification information by which contents of a captured image are identified can be added to the image data. The term "identification information" used herein includes ID of the user who has captured the image, ID of a subject, a date and time on which the image was captured, information about the number of captured images (a value indicated by a counter), and an image quality determination result. The identification information can be transmitted from a control device 200 prior to switching of an imaging mode, or can be input by operation of a body of the radiographic apparatus 100. When a plurality of subjects is successively photographed, the radiographic apparatus 100 can receive information including a list of the subjects to be radiographed from the control device 200 beforehand. In this way, the radiographic apparatus 100 can link the received information about the subject to be radiographed to a captured image and identification information.

The image data stored in the storage unit is transferred to the control device 200 when the radiographic apparatus 100 is connected to the control device 200 subsequent to the image capturing. In this process, all of the image data can be automatically transferred, or image data to be transferred can be selected. Alternatively, the image data can be transferred to an external storage device, such as a universal serial bus (USB) memory, a secure digital (SD) card, or a hard disk drive, connected to the radiographic apparatus 100.

If the stand-alone mode is not used, captured-image data is successively transferred to the control device 200.

Figure 8:
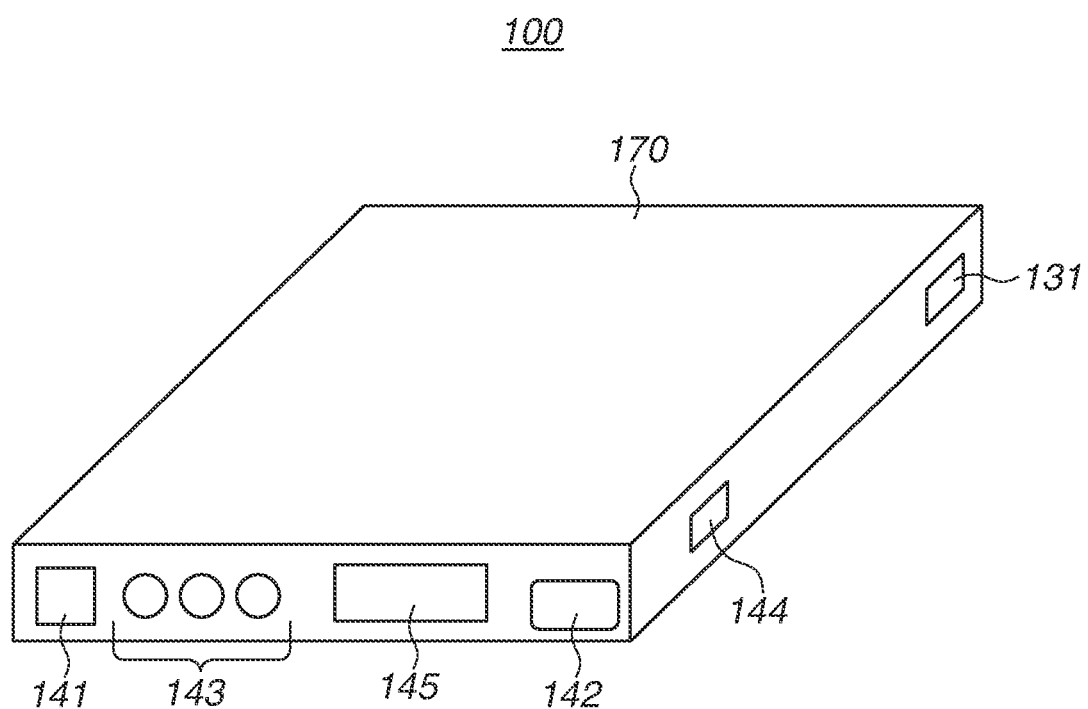
FIG. 8 is a diagram illustrating an exemplary external configuration of the radiographic apparatus.

FIG. 8 is a schematic diagram illustrating an exemplary external configuration of the radiographic apparatus 100.

When an image is captured in a stand-alone mode, an external notifying unit such as a control device 200 cannot be used. Thus, the use of an extra notifying unit is needed for a user to confirm a state of the radiographic apparatus 100 compared to a system other than a system including the external notifying unit. Since the user cannot check an image immediately after the image is captured, a notifying unit enabling the user to readily confirm that the image has been captured is necessary. Information indicating the number of captured images can be displayed on an LCD counter 145, so that the user can confirm that the image has been captured. The LCD counter 145 can display, for example, error information of the radiographic apparatus 100. The LCD counter 145 can notify the user of a state in which the radiographic apparatus 100 has become ready for image capturing, or a state in which the radiographic apparatus 100 has become unable to capture an image. If there is time limit on a state in which an image can be captured, the user can be notified of information such as a remaining time by a counter display or sound.

When an image is captured in the stand-alone mode, a speaker performs notification at a time when radiation irradiation is detected so that the user can reliably confirm that an image has been captured even in a state in which the user cannot check the LCD counter 145. When an image is not captured in the stand-alone mode, the user is notified of necessary information by one or more of the speaker and the LCD.

According to the above-described exemplary embodiments, the radiographic apparatus can switch a notifying unit to an optimally suitable notifying unit based on conditions or an environment in which an image is captured so that a user can be notified of necessary information at appropriate timing, and thus, an incorrect operation is prevented and usability is enhanced.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-217078, filed Nov. 7, 2016, which is hereby incorporated by reference herein in its entirety.

What is claimed is:

1. The radiographic apparatus comprising:
a plurality of notifying units, each including a different way to provide notification;
a switching unit configured to switch at least one of the plurality of notifying units to be used to provide notification; and
a storage unit configured to store captured image data,
wherein the radiographic apparatus includes a plurality of imaging modes,
wherein the switching unit switches at least one of the plurality of notifying units to be used based on an imaging mode to be used,
wherein the plurality of notifying units includes a first notifying unit configured to perform notification using light and a second notifying unit configured to perform notification using sound,
wherein the plurality of imaging modes includes a first imaging mode in which the radiographic apparatus captures images while successively storing the captured image data in the storage unit without transferring the captured image data to an external device and a second imaging mode in which the radiographic apparatus captures images while successively transferring the captured image data to the external device, and
wherein both the first notifying unit and the second notifying unit are used in the first imaging mode and at least one of the first notifying unit and the second notifying unit is used in the second imaging mode.

2. The radiographic apparatus according to claim 1, wherein, in the second imaging mode, the captured image data is transferred to the external device and stored in the storage unit.

3. The radiographic apparatus according to claim 1, wherein the first notifying unit includes a counter that displays information associated with a number of captured images.

4. The radiographic apparatus according to claim 1, wherein the second notifying unit includes a speaker that make a sound indicating a state in which the radiographic apparatus has become ready for image capturing or a state in which the radiographic apparatus has become unable to capture an image.

5. The radiographic apparatus comprising:
a plurality of notifying units, each including a different way to provide notification;
a switching unit configured to switch at least one of the plurality of notifying units to be used to provide notification; and
a detector configured to detect start of radiation irradiation,
wherein the radiographic apparatus includes a plurality of imaging modes,
wherein the switching unit switches at least one of the plurality of notifying units to be used based on an imaging mode to be used,
wherein the plurality of notifying units includes a first notifying unit configured to perform notification using light and a second notifying unit configured to perform notification using sound,
wherein the plurality of imaging modes includes a first imaging mode in which the radiographic apparatus captures an image based on a determination by the detector that radiation irradiation has started and a second imaging mode in which the radiographic apparatus captures an image in response to receipt of an irradiation start signal from a radiation generating device, and
wherein both the first notifying unit and the second notifying unit are used in the first imaging mode and at least one of the first notifying unit and the second notifying unit is used in the second imaging mode.

6. The radiographic apparatus comprising:
a plurality of notifying units, each including a different way to provide notification;
a switching unit configured to switch at least one of the plurality of notifying units to be used to provide notification,
wherein the radiographic apparatus includes a plurality of imaging modes,
wherein the switching unit switches at least one of the plurality of notifying units to be used based on an imaging mode to be used,
wherein the plurality of notifying units includes a first notifying unit configured to perform notification using light and a second notifying unit configured to perform notification using sound,
wherein the radiographic apparatus includes an auto exposure control function of stopping radiation irradiation when a dose of radiation reaches a predetermined dose,
wherein the plurality of imaging modes includes a first imaging mode in which the radiographic apparatus captures an image using the auto exposure control function and a second imaging mode in which the radiographic apparatus captures an image without using the auto exposure control function, and
wherein the second notifying unit is used in the first imaging mode, and the at least one of the first notifying unit and the second notifying unit is used in the second imaging mode.

7. The radiographic apparatus comprising:
a plurality of notifying units, each including a different way to provide notification;
a switching unit configured to switch at least one of the plurality of notifying units to be used to provide notification; and
at least one of an optical sensor and a pressure sensor,
wherein the switching unit switches at least one of the notifying units to be used based on a signal output from the at least one of the optical sensor and the pressure sensor.

8. A radiographic system comprising:
a radiographic apparatus; and
a control device configured to perform image processing on image data acquired from the radiographic apparatus,
wherein the radiographic apparatus comprises:
a plurality of notifying units, each including a different way to provide notification, and
a switching unit configured to switch at least one of the plurality of notify units to be used to provide notification; and
a storage unit configured to store captured image data,
wherein the radiographic apparatus includes a plurality of imaging modes,
wherein the switching unit switches at least one of the plurality of notifying units to be used based on an imaging mode to be used,
wherein the plurality of notifying units includes a first notifying unit configured to perform notification using light and a second notifying unit configured to perform notification using sound,
wherein the plurality of imaging modes includes a first imaging mode in which the radiographic apparatus captures images while successively storing the captured image data in the storage unit without transferring the captured image data to an external device and a second imaging mode in which the radiographic apparatus captures images while successively transferring the captured image data to the external device, and
wherein both the first notifying unit and the second notifying unit are used in the first imaging mode and at least one of the first notifying unit and the second notifying unit is used in the second imaging mode.

9. The radiographic system according to claim 8, wherein, in the second imaging mode, the captured image data is transferred to the external device and stored in the storage unit.

10. The radiographic system according to claim 8, wherein the first notifying unit includes a counter that displays information associated with a number of captured images.

11. The radiographic apparatus according to claim 8, wherein the second notifying unit includes a speaker that make a sound indicating a state in which the radiographic apparatus has become ready for image capturing or a state in which the radiographic apparatus has become unable to capture an image.

* * * * *